United States Patent [19]
Willing

[11] Patent Number: 5,356,389
[45] Date of Patent: Oct. 18, 1994

[54] INFUSION NEEDLE

[76] Inventor: Erika Willing, Emil-von-Behring Str. 17, 4290 Bocholt, Fed. Rep. of Germany

[21] Appl. No.: 42,807

[22] Filed: Apr. 5, 1993

[30] Foreign Application Priority Data

Apr. 9, 1992 [DE] Fed. Rep. of Germany ....... 4211932

[51] Int. Cl.⁵ ........................................ A61M 5/178
[52] U.S. Cl. ................... 604/164; 604/165; 604/264
[58] Field of Search ............ 604/164, 158, 165, 161, 604/162, 171, 174, 177, 264, 272, 280; 128/DIG. 26

[56] References Cited

U.S. PATENT DOCUMENTS

| | | | |
|---|---|---|---|
| 2,008,340 | 7/1935 | Salvati et al. | 604/174 |
| 2,402,306 | 6/1946 | Turkel | 604/174 |
| 3,900,026 | 8/1975 | Wagner | 604/174 |
| 4,292,970 | 10/1981 | Hession | 604/158 |
| 4,392,853 | 7/1983 | Muto | 604/171 |
| 4,518,383 | 5/1985 | Evans | 604/272 |
| 4,690,675 | 9/1987 | Katz | 604/177 |
| 4,846,805 | 7/1989 | Sitar . | |
| 5,163,913 | 11/1992 | Rantanen-Lee et al. | 604/177 |

FOREIGN PATENT DOCUMENTS

| | | |
|---|---|---|
| 9101636.3 | 6/1991 | Fed. Rep. of Germany . |
| 3539243 | 12/1991 | Fed. Rep. of Germany . |
| 2245383 | 5/1973 | France . |
| 8807388 | 10/1988 | PCT Int'l Appl. . |
| 400463 | 4/1966 | Switzerland . |

Primary Examiner—John G. Weiss
Attorney, Agent, or Firm—Meltzer Lippe Goldstein, Wolf, Schlissel & Sazer

[57] ABSTRACT

An infusion needle, more particularly for general infusion therapy, having a needle body (1) having a metal cannula (2) and a cylindrical receiving opening (3) connected thereto, the best possible adaptation to movements by the patient is achieved, without having to abandon the secure retention of the infusion needle at the place of application, by the features that the metal cannula (2) takes the form of an inner aspiration needle which is enclosed by a somewhat shorter closely adjoining plastics cannula (4) which terminates conically and is connected to the receiving opening (3), the needle body (1) being constructed bent in the transitional zone between the receiving opening (3) and the plastics cannula (4), and the metal cannula (2) being constructed to be drawn out of the enclosing plastics cannula (4) and the needle body (1).

8 Claims, 1 Drawing Sheet

INFUSION NEEDLE

BACKGROUND OF THE INVENTION

The invention relates to an infusion needle, more particularly for general infusion therapy, having a needle receiving body having a metal cannula and a cylindrical receiving opening connected thereto for receiving applicators, the metal cannula taking the form of an aspiration needle which is enclosed by a somewhat shorter, closely adjoining plastics cannula which terminates conically and is connected to the receiving opening.

In addition to the oral and rectal administration of medicaments, parenteral administration forms one of the bases of present-day therapy. Even though in modern medicine intravenous infusion therapy and arterial injection techniques have partly displaced injection therapy in its three classical forms—i.e., the subcutaneous, intramuscular and intravenous administration of medicaments—, subcutaneous and intracutaneous administration still form a wide range of infusion therapy, more particularly for the treatment of pain and diabetes. They developed in many small steps and over a prolonged period. Methods for bleeding and the supply of medicaments have been known for many years.

The discovery of the circulation of the blood at the beginning of the 17th century created the anatomical and physiological basis for infusion and transfusion. Even at that time the first infusion experiments began, at first on animals and subsequently on human beings also. At first they were unable to achieve any therapeutic effect or any progress in knowledge. Since the reason for the initial failures was probably mainly septic conditions, the invention of the injection syringe in the 19th century first opened up the way to modern injection and infusion therapy. However, a new chapter in the theory of transfusion began only after the discovery of blood groups at the beginning of the present century. Only then could those decisive foundations and techniques be developed which, encouraged by the two world wars and the development of internal medicine and anaesthesiology, are still for the most part valid at the present day.

Subcutaneous injection still plays an important role in the field of pain therapy, although therapeutic subcutaneous injections are a good deal less frequent than they used to be. This decline is partly due to the fact that resorption times are difficult to determine and depend heavily on the state of the particular patient. On the other hand, nowadays more different agents are injected which are incompatible when applied subcutaneously. Nevertheless, subcutaneous techniques, more particularly subcutaneous infusions are still important, more particularly for children. In the case of subcutaneous infusion it is very important for the infusions to be performed in accordance with the laws of the art, since injection into the skin not only causes severe pain, but may lead to violent inflammations, even including skin necroses. Subcutaneous injection is also known to be followed by oedematous swellings accompanied by varying degrees of inflammation, so that the sense of well-being of the patients is often very adversely affected. However, these complications are usually harmless and disappear in a few days. However, in rare cases they may also lead to skin necrosis and via secondary infection to erysipelas and, if the patient's initial condition is unfavourable, to sopsis. Even today, intracutaneous injection still plays an important role in BCG protective inoculation (Bacille-Calmette-Guerin; protective inoculation against tuberculosis). It is frequently used in curative therapy.

In subcutaneous injection or infusion the medicament must be administered by injection into the subcutaneous fatty tissue, while in intracutaneous injection a deposit of medicament comes to lie directly in the skin (cutis). The majority of subcutaneous injections are administered in the zone of the upper arm, the thigh or the chest. In contrast with other injection methods, in subcutaneous injection technique there is no essential difference between the application of this therapy to men, women, children or sucklings.

Whereas in the case of injection the injection needle is after the depositing of a medicament withdrawn from the subcutaneous or intracutaneous tissue, an infusion needle remains at the place of application for a prolonged period, possibly of up to several days. It can quickly be seen that this is unpleasant for the patient, whose freedom of movement is thereby impeded. Unavoidable movements can cause various degrees of pain.

CH-PS 400 463 discloses a cannula for infusions, more particularly for continuous drip infusions, having a needle receiving body having a metal cannula and a cylindrical receiving opening connected thereto. In that known needle the metal cannula takes the form of an aspiration cannula enclosed by a somewhat shorter, closely adjoining plastics cannula which terminates conically and is connected to the receiving opening. This known infusion needle has a metal cannula which comes to lie at a small angle to the surface of the skin in the subcutaneous or intracutaneous tissue. Even if the known infusion needle can be simply attached to the skin, due to the bend it stands out relatively high and therefore chafes, for example, against the patient's clothing, something which again may cause the patient pain.

It is therefore an object of the invention so to design and further develop the infusion needle described in greater detail hereinbefore that the best possible adaptation to the patient's movements is achieved, without having to abandon the secure retention of the infusion needle at the place of application.

SUMMARY OF THE INVENTION

This problem is solved according to the invention by the features that the needle receiving body is constructed bent in the transitional zone between the receiving opening and the plastics cannula, and the metal cannula is constructed to be drawn out of the enclosing plastics cannula and the needle receiving member.

The invention provides an infusion needle in which the metal cannula is required solely for the actual injection. After the injection of the infusion needle and its attachment at the place of application, the metal cannula, the so-called mandrel, as in the case of "Braunüle" (registered Trade Mark of B. Braun Melsungen AG-)—is removed from the enclosing plastics cannula. Relative movements of the subcutis in relation to the epidermis are now substantially pain-free to the patient, since the flexible plastics cannula can adapt itself to such relative movements without substantially changing its position. The bend in the infusion needle according to the invention ensures that the receiving opening of the needle receiving member extends substantially parallel with the surface of the skin. The bend should be between 15° and 25°. An angle of 20° has proved particularly advantageous.

According to a further feature of the invention the transitional zone between the cylindrical receiving opening and the plastics cannula is constructed conical. This ensures that during the production of the infusion needle the mandrel cannot damage the plastics cannula when it is introduced thereinto, and moreover an even bending of the mandrel is rendered possible in the bent transitional zone between the receiving opening and the plastics cannula.

According to another feature of the invention in the zone of bend the needle receiving body has a plane widened portion, and on the side having the plastics cannula the widened portion has a resilient support. It has been found to be a particularly convenient feature that the resilient support provided is an endless foamed plastics strip extending along the edges of the widened portion. Such a resilient support is already known from so-called "gripper" needles, such as are used with fully implantable catheter systems.

Particularly conveniently at its end remote from the tip of the needle the metal cannula has a receiving element having an integral holding plate. This ensures that the infusion needle according to the invention can be safely handled during injection.

According to another feature of the invention the needle receiving body has in the zone of the receiving opening and/or the receiving element of the metal cannula means which prevent any axial rotation of the introduced metal cannula. In dependence on the kind of aspiration, this feature ensures the required firm association between the obliquely ground metal cannula tip and the needle receiving body.

BRIEF DESCRIPTION OF THE DRAWINGS

There are various possible ways of putting into effect and further developing the teaching of the invention, in which respect attention is drawn on the one hand to the subclaims and on the other hand to the following explanation of a preferred embodiment of the infusion needle according to the invention, with reference to the drawings, wherein:

DETAILED DESCRIPTION OF THE INVENTION

Figure 1:
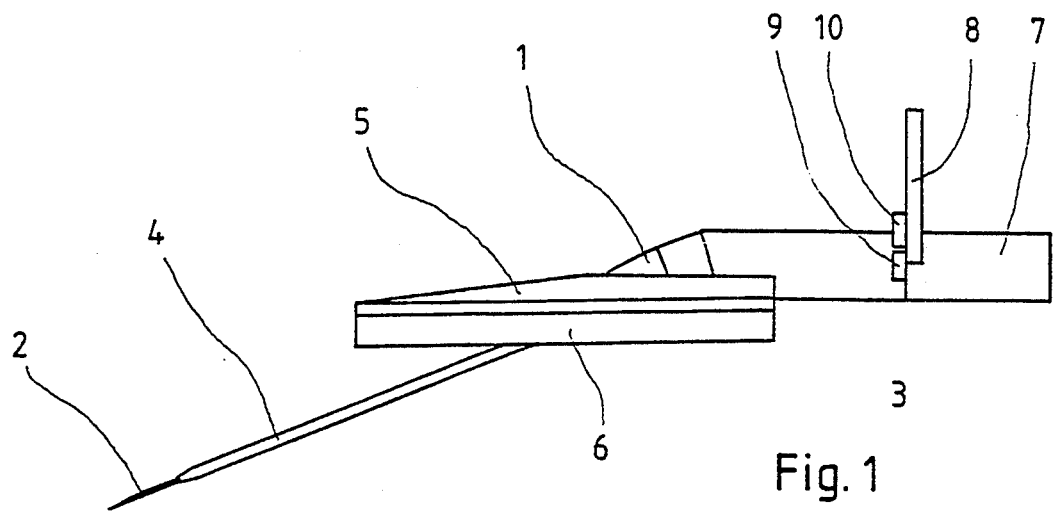
FIG. 1 is a side elevation of the infusion needle according to the invention.
Figure 2:
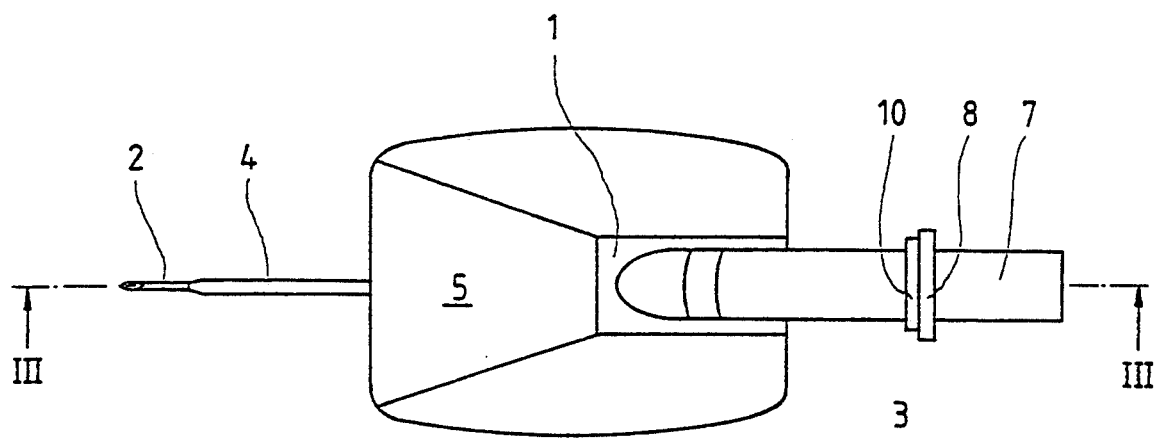
FIG. 2 is a plan view of the injection needle according to the invention.

FIGS. 1 and 2 show an infusion needle according to the invention having a needle receiving body 1 which has in the first place a metal cannula 2 and a cylindrical receiving opening 3 connected thereto. The metal cannula 2 takes the form of an inner aspiration cannula and is enclosed by a shorter plastics cannula 4 which bears closely thereagainst and which terminates conically and is connected to the receiving opening 3.

Figure 3:
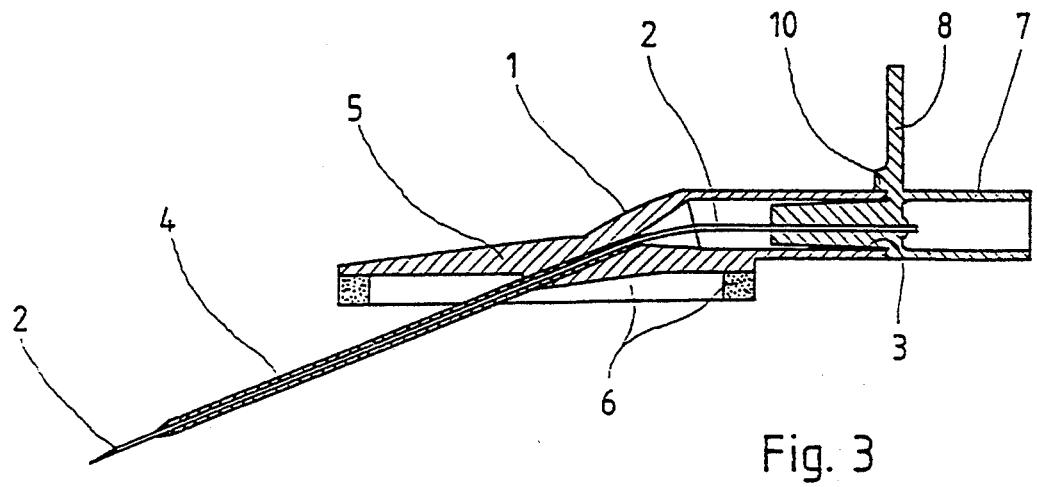
FIG. 3 is a longitudinal section, taken along the line III-III in FIG. 2, through the injection medium according to the invention.

FIG. 3 shows in longitudinal section the infusion needle according to the invention as shown in FIG. 1. FIG. 3 clearly shows the design of the receiving opening 3. The infusion needle according to the invention is characterized in that the metal cannula 2 takes the form of an aspiration cannula enclosed by a somewhat shorter plastics cannula which bears closely thereagainst and which terminates conically and is connected to the receiving aperture 3; the needle receiving body 1 is constructed bent in the transitional zone between the receiving opening 3 and the plastics cannula 4; and the metal cannula 2 is constructed to be drawn out of the enclosing plastics cannula 4 and the needle receiving body 1. As already mentioned, advantageously the bend amounts to between 15° and 25°. An angle of 20° is provided in the preferred embodiment illustrated.

FIG. 3 also shows how the transitional zone between the cylindrical receiving opening 3 and the plastics cannula 4 is constructed conical. This on the one hand facilitates the introduction of the metal cannula 2 and the plastics cannula 4, while on the other hand the metal cannula 2 acquires adequate free space for its bending as required by the bent portion.

For the attachment of the infusion needle according to the invention to the place of application, in the zone of the bend the needle receiving body 1 has a plane widened portion 5. As can be gathered more particularly from FIGS. 1 and 3, the widened portion 5 has on the underside of the needle receiving body 1, having the plastics cannula 4, a resilient support which preferably takes the form of an endless foamed plastic strip 6 extending along the edges of the widened portion 5.

The drawings also show how the metal cannula 2 has at its end remote from the cannula tip a receiving element 7 having an integral holding plate 8. This enables a medicament to be injected already through the applied metal cannula 2. Lastly, to facilitate handling, the needle receiving body 1 has in the zone of the receiving opening 3, and the receiving element 7 of the metal cannula 2 also has means for preventing axial rotation of the introduced metal cannula 2. For this purpose the needle receiving body 1, as shown in FIG. 1. has lateral projections 9, the receiving element 7 having a web 10 after the fashion of a segment of a ring. This is indispensable for safe handling, since in the zone of its tip the metal cannula 2 is constructed chamfered at a small angle, to ensure regular penetration into the skin. After the infusion needle has been applied, the needle receiving body 1 rests via the widened portion 5 having the resilient support 6 on the surface of the patient's skin. After fixing has been successfully achieved at that place, the mandrel 2 can be drawn out of the plastics cannula 4 and a suitable applicator can be connected to the receiving opening 3 of the needle receiving body 1.

The drawings show clearly that after the mandrel 2 has been withdrawn, including the receiving element 7 and the holding plate 8, the whole needle receiving body 1 rises only very slightly, namely substantially only by the height of the external dimension of the needle receiving body 1 in the zone of the receiving opening 3, since the foamed plastics strip 6 is still compressed by its fixation at the place of application.

I claim:
1. An infusion needle comprising
   a needle receiving body comprising a first portion having a cylindrical receiving opening therein and a transition zone,
   a plastic cannula which passes through said transition zone, said plastic cannula having a conically shaped first end which terminates at and is connected to said receiving opening and a second end extending away from the transition zone,
   said first portion being constructed with a bend therein so that an angle is formed between said transition zone and said receiving opening of said body, and so that said plastic cannula emerges from said body at substantially said angle with respect to said first portion, and a metal cannula which passes through and is removably received within said cylindrical receiving opening of said body and within said plastic cannula, said metal cannula being longer than said plastic cannula so that said metal cannula extends beyond said second end of said plastic cannula.

2. The infusion needle of claim 1 wherein said angle is between 15° and 25°.

3. The infusion needle of claim 1 wherein said angle is about 20°.

4. The infusion needle of claim 1 wherein said transition zone has a conical shape.

5. The infusion needle of claim 1 wherein said transition zone has a plane widened portion, and wherein said widened portion has a resilient support in the region of said plastic cannula.

6. The infusion needle of claim 5 wherein said resilient support comprises an endless foam plastic strip extending along edges of said widened portion.

7. The infusion needle of claim 1 wherein said metal cannula has a receiving element with an integral holding plate in the region of said cylindrical receiving opening.

8. The infusion needle of claim 7 wherein said needle receiving body includes means for preventing axial rotation of said metal cannula.

* * * * *